United States Patent

Pohl et al.

[11] Patent Number: 6,107,493
[45] Date of Patent: Aug. 22, 2000

[54] PREPARATION OF CYCLIC PERFLUOROALKANEBIS (SULFONYL) IMIDES

[75] Inventors: Ludwig Pohl, Darmstadt; Volker Hilarius, Gross-Umstadt; Peter Sartori, Rheinberg; Ralf Jueschke, Duisburg, all of Germany

[73] Assignee: Merck Patent Gesellschaft mit Beschrankter Haftung, Germany

[21] Appl. No.: 09/125,949

[22] PCT Filed: Feb. 20, 1997

[86] PCT No.: PCT/EP97/00819

§ 371 Date: Nov. 12, 1998

§ 102(e) Date: Nov. 12, 1998

[87] PCT Pub. No.: WO97/31909

PCT Pub. Date: Sep. 4, 1997

[30] Foreign Application Priority Data

Jan. 1, 1996 [DE] Germany .............................. 196 07 832

[51] Int. Cl.[7] .......................... C07D 205/04; H01M 6/04
[52] U.S. Cl. ............................................ 548/952; 429/198
[58] Field of Search ............................... 548/952; 429/198

[56] References Cited

U.S. PATENT DOCUMENTS

| 4,429,093 | 1/1984 | Koshar . |
| 5,021,308 | 6/1991 | Armand et al. . |
| 5,652,072 | 7/1997 | Lamanna et al. ....................... 429/198 |

FOREIGN PATENT DOCUMENTS

| 0 057 327 | 8/1982 | European Pat. Off. . |
| 88 03331 | 5/1988 | WIPO . |

OTHER PUBLICATIONS

F. Dallacker, *Justus Liebigs Annalen Der Chemie*, vol. 689, pp. 179–188 (Dec. 3, 1965).

D. Viets et al., *Chemische Berichte*, vol. 124, No. 6, pp. 1353–1356 (Jun. 6, 1991).

*Primary Examiner*—Deborah C. Lambkin
*Attorney, Agent, or Firm*—Millen, White, Zelano & Branigan, P.C.

[57] ABSTRACT

The invention relates to a process for the preparation of cyclic perfluoroalkanebis(sulfonyl)imides and salts thereof.

The new compound lithium cyclo-difluoromethanebis(sulfonyl)imide is outstandingly suitable as a conductive salt in non-aqueous electrolytes for lithium secondary batteries.

13 Claims, No Drawings

PREPARATION OF CYCLIC PERFLUOROALKANEBIS (SULFONYL) IMIDES

This appln is a 371 of PCT/EP97/00819 Feb. 20, 1997.

The invention relates to a process for the preparation of cyclic perfluoroalkanebis(sulfonyl)imides and salts thereof.

Cyclic perfluoroalkanebis(sulfonyl)imides, and salts of these compounds, which contain at least two ring carbon atoms are known from EP 0 057 327 B1. Compounds of this type can be obtained from corresponding open-chain precursors by a cyclization reaction. According to the patent specification mentioned, the compounds are prepared by passing gaseous ammonia through a solution of a corresponding perfluoroalkane-bis-sulfonyl fluoride. Ring compounds which are initially obtained in the form of the ammonium salts are formed by this procedure. The imides or imide salts with other cations can be obtained by an exchange reaction.

It is known from WO 88/03331 that cyclic perfluoroalkanebis(sulfonyl)imide salts prepared in this way, such as, in particular, the corresponding lithium salts, can be employed as conductive salts in non-aqueous electrolytes for lithium secondary batteries.

It can be seen from EP 0 057 327 B1 that the preparation process described therein gives only product yields which are not very satisfactory. Our studies confirm this, and furthermore show that the target products are obtained in a form contaminated with undesirable by-products and other impurities, from which they can be separated off only with difficulty and with further losses in yield. However, a high and reproducible purity of these compounds is of essential importance for use as a constituent of battery electrolytes.

SUMMARY OF THE INVENTION

It has now been found that cyclic perfluoroalkanebis (sulfonyl)imides and salts thereof can be obtained in a virtually quantitative yield and in a form which is largely free from by-products and impurities if a solution of the corresponding perfluoroalkane-bis-sulfonyl fluoride is metered slowly and with intensive thorough mixing into liquid ammonia.

It has furthermore been found that the compound cyclo-difluoromethanebis(sulfonyl)imide, which is new per se, and salts thereof can be obtained by the process according to the invention.

The invention thus relates to a process for the preparation of cyclic perfluoroalkanebis(sulfonyl)imides and salts thereof by a cyclization reaction of corresponding perfluoroalkane-bis-sulfonyl fluorides in which a solution of the perfluoroalkane-bis-sulfonyl fluoride is metered slowly and with intensive thorough mixing into liquid ammonia.

The invention furthermore relates to the new ammonium and lithium salts of cyclo-difluoromethanebis(sulfonyl) imide.

The invention moreover relates to the use of lithium cyclo-difluoromethanebis(sulfonyl)imide as a conductive salt in non-aqueous electrolytes for lithium secondary batteries.

The invention finally relates to non-aqueous electrolytes for lithium secondary batteries which comprise the compound lithium cyclo-difluoromethanebis(sulfonyl)imide, and lithium secondary batteries which comprise such electrolytes.

The process according to the invention starts from the same non-cyclic starting compounds and is based in principle on the same cyclization reaction as the known processes. However, an essential difference is that in this case the starting compound is cyclized in and at the temperature of liquid ammonia, the reaction partner ammonia always being present in excess in the course of the reaction because of the reaction conditions chosen. The formation of by-products and impurities is presumably largely suppressed by this excess ammonia and the low reaction temperature.

Liquid ammonia is produced in a manner known per se by condensation of ammonia gas with appropriate cooling. The temperature of the liquid ammonia is −70° C. or even lower. Cooling which is suitable for the laboratory to pilot plant scale can be effected with the aid of dry ice (solid carbon dioxide), mezhanol/dry ice refrigerating mixtures or with liquid nitrogen. The liquefaction is carried out by condensing the ammonia gas into the cooled reaction vessel.

The perfluoroalkanebis(sulfonyl)imide is employed in the form of a solution in a suitable organic solvent. Tetrahydrofuran (THF) has proved favorable as the solvent. It is expedient also to take up the liquid ammonia condensate in THF. For carrying out the cyclization reaction, the solution of the starting substance is metered slowly and with intensive thorough mixing into the liquid ammonia or its THF solution. The addition can be carried out in small portions, for example by dropwise addition, and the thorough mixing can be carried out by stirring the reaction mixture. It is to be ensured here that the reaction mixture is kept at the temperature of the liquid ammonia and corresponding heat of reaction is removed by cooling. When the reaction has ended and the excess ammonia has been evaporated off, the target product can be obtained in the form of the corresponding ammonium salt by extracting the residue with THF and removing the solvent. The reaction yield is high to virtually quantitative. As a rule, further purification operations are not necessary.

The ammonium cyclo-perfluoroalkanebis(sulfonyl) imides thus obtained can be converted into the corresponding imides or into other metal salts by a simple exchange reaction. Conversion into corresponding lithium salts by reaction with lithium hydroxide is of particular interest. This reaction also proceeds virtually quantitatively without the formation of by-products and impurities.

For this reaction, for example, the ammonium compound is boiled with lithium hydroxide monohydrate in THF until no further ammonia forms.

The yield is also virtually quantitative in this process step.

It is surprising that the homologous 4-membered ring compounds, which have not hitherto been described, can be obtained by the process according to the invention. These are the compounds cyclo-difluoromethanebis(sulfonyl) imide and the corresponding ammonium and lithium salts.

Against generally accepted expectations, it has furthermore been found that the abovementioned 4-membered ring compounds are exceptionally stable. Thus, no decomposition occurs during dry storage at a temperature of 100° C. Only from temperatures above 230° C. are slight yellow discolorations of the otherwise colourless material found after several hours. Also after storage in solution, for example in organic solvents, such as THF or acetonitrile, no changes in colour can be found and no decomposition products are to be detected even after weeks.

For this reason alone, the new compound lithium cyclo-difluoromethanebis(sulfonyl)imide according to the invention is outstandingly suitable as a conductive salt in non-aqueous electrolytes for lithium secondary batteries.

In addition to organolithium salts, as the abovementioned compound is, such electrolytes comprise one or more non-aqueous organic solvents and, if appropriate, further additives. Further details on such electrolytes and the build-up and mode of Functioning of lithium secondary batteries are known to the relevant expert. The compound according to the invention can be employed in complete analogy to the lithium compounds known for this use. The compound according to the invention likewise shows an exceptional stability here. The corresponding battery cells show outstanding properties in respect of capacity and constant voltage and unrestricted functional capacity over an above-average high number of charging-discharging cycles.

EXAMPLE 1

Ammonium cyclo-perfluoroalkane-1,n-bis(sulfonyl) imides 55 ml of anhydrous ammonia are condensed through a gas inlet tube into a two-necked flask of 250 ml capacity which is cooled with dry ice and provided with an intensive cooler (temperature −70° C.). Thereafter, the inlet tube is replaced by a dropping funnel and 55 ml of dry THF are added dropwise.

A solution of 200 mmol of the particular perfluoroalkane-1,n-bis(sulfonyl fluoride) (n=1–3) in 100 ml of THF are then slowly added dropwise (120 minutes) to the THF-ammonia solution, while stirring. During the dropwise addition, the reaction flask is cooled further with dry ice.

During the exothermic reaction, the ammonium fluoride which forms and also some of the ammonium imide formed precipitate out. When the reaction has ended, the ammonia which remains is allowed to evaporate by warming the suspension to room temperature. The precipitate is extracted with 100 ml of THF over a frit.

The combined THF solutions are freed from the solvent by distillation and the colorless solid which remains is dried in vacuo at 40° C.

TABLE 1

Ammonium cyclo-perfluoroalkane-1,n-bis-(sulfonyl)imides (n = 1 – 3)

| n | $m_{educt}$ [g] | Yield [g] | $M_{product}$ [g mol$^{-1}$] | Empirical formula |
|---|---|---|---|---|
| 1 | 43.22 | 29.42 g or 70% | 210.17 | $CH_4F_2N_2O_4S_2$ |
| 2 | 53.23 | 44.75 g or 86% | 260.18 | $C_2H_4F_4N_2O_4S_2$ |
| 3 | 63.23 | 50.25 g or 81% | 310.19 | $C_3H_4F_6N_2O_4S_2$ |

EXAMPLE 2

Lithium cyclo-perfluoroalkane-1,n-bis(sulfonyl) imides 4.6 g (110 mmol) of lithium hydroxide monohydrate are added to a solution of 100 mmol of the corresponding ammonium cyclo-perfluoroalkane-1,n-bis(sulfonyl)imide in 60 ml of THF, while stirring. The suspension is boiled until no further evolution of ammonia can be detected (about 120 mins). After filtration of the reaction solution and removal of the solvent, the solid which remains is taken up in water and boiled with active charcoal (about 180 mins).

Thereafter, the suspension is filtered, the water is stripped off and the colorless solid which remains is dried under a high vacuum. This solid is then dissolved again in 50 ml of anhydrous THF, the solution is filtered and the solvent is removed again.

In order to free the lithium imides from still-adhering THF residues, these are suspended three times in 50–60 ml of n-pentane, the solvent being removed again each time.

The lithium cyclo-perfluoroalkane-1,n-bis(sulfonyl) imides are then dried on a water bath under a high vacuum for 8 hours. Colorless, crystalline salts are obtained.

TABLE 2

Lithium cyclo-perfluoroalkane-1,n-bis-(sulfonyl)imide (n = 1 – 3)

| n | $m_{educt}$ [g] | Yield [g] | $M_{product}$ [g mol$^{-1}$] | Empirical formula |
|---|---|---|---|---|
| 1 | 21.02 | 19.31 g or 97% | 199.07 | $CF_2LiNO_4S_2$ |
| 2 | 26.02 | 24.16 g or 97% | 249.08 | $C_2F_4LiNO_4S_2$ |
| 3 | 31.02 | 28.71 g qr 96% | 299.09 | $C_3F_6LiNO_4S_2$ |

Lithium cyclo-difluoromethane-1,1-bis(sulfonyl) imide

Lithium content: found: 3.49% calculated: 3.49%

$^{13}$C-NMR(CD$_3$CN, 75.4 MHz, total): δ=133.94 (t, $^1J_{CF}$=366.9 Hz)

$^{19}$F-NMR(CD$_3$CN, C$_6$F$_6$ external), 75.4 MHz): δ=−86.95 (s)

Lithium cyclo-tetrafluoroethane-1,2-bis(sulfonyl) imide

Lithium content: found: 2.80% calculated: 2.790%

$^{13}$C-NMR(CD$_3$CN, 125.76 MHz, 30% by weight): δ=115.58 (tt, $^1J_{CF}$=306.6 Hz), $^2J_{CF}$=22.6 Hz)

$^{19}$F-NMR (CD$_3$CN, C$_6$F$_6$ external), 75.4 MHz, 30% by weight): δ=−113.72(s)

Lithium cyclo-hexafluoropropane-1,3-bis(sulfonyl) imide

Lithium content: found: 2.31% calculated: 2.31%

$^{13}$C-NMR(CD$_3$CN, 125.76 MHz, 30% by weight): δ=110.72 (tqi, $^1J_{CF}$=273.0 HZ), $^2J_{CF}$=25.5 Hz), 113.96 (tt, $^1J_{CF}$=298.1 Hz), $^2J_{CF}$=25.3 Hz)

$^{19}$F-NMR(CD$_3$CN, C$_6$F$_6$ external) 75.4 MHz, 30% by weight): δ=−125.21

(qi, $^3J_{FF}$=8.6 Hz), −118.77 (t, $^{J3}_{FF}$=8.5 Hz)

What is claimed is:

1. A process for the preparation of a cyclic perfluoroalkanebis(sulfonyl)imide or a salt thereof comprising cyclizing a corresponding perfluoroalkane-bis-sulfonyl fluoride in liquid ammonia.

2. A process according to claim 1, wherein the perfluoroalkane-bis-sulfonyl fluoride is dissolved in THF.

3. A process according to claim 1, further comprising converting the cyclic perfluoroalkanebis(sulfonyl)imide ammonium salt initially obtained into a corresponding imide or into another metal salt by an exchange reaction.

4. A process according to claim 3, wherein the cyclic perfluoroalkanebis(sulfonyl)imide ammonium salt is reacted with lithium hydroxide to obtain the corresponding lithium salt.

5. A process according to claim 1, comprising converting difluoroalkanebis-sulfonyl imide ammonium salt into ammonium cyclodifluoromethanebis(sulfonyl)imide.

6. A process according to claim 5, further comprising reacting ammonium cyclo-difluoromethanebis(sulfonyl) imide with lithium hydroxide to give lithium cyclo-difluoromethanebis-(sulfonyl)imide.

7. Ammonium cyclo-difluoromethanebis(sulfonyl)imide or lithium cyclo-difluoromethanebis(sulfonyl)imide.

8. Lithium cyclo-difluoromethanebis(sulfonyl)imide.

9. A lithium secondary battery comprising a non-aqueous electrolyte containing a compound according to claim 8.

10. A non-aqueous electrolyte, comprising a lithium salt, which is the compound according to claim 8.

11. A process according to claim 1, further comprising formulating a non-aqueous electrolyte from the cyclic perfluoroalkanebis(sulfonyl)imide.

12. A process according to claim 9, further comprising introducing said electrolyte into a lithium secondary battery.

13. A process according to claim 1, wherein a solution of the perfluoroalkane-bis-sulfonyl fluoride is metered slowly and with intensive thorough mixing into fluoride in liquid ammonia.

* * * * *